US012336831B2

(12) United States Patent
Ko et al.

(10) Patent No.: US 12,336,831 B2
(45) Date of Patent: Jun. 24, 2025

(54) NON-INVASIVE TYPE ELECTROCARDIOGRAM MONITORING DEVICE AND METHOD

(71) Applicants: INDUSTRY—ACADEMIC COOPERATION FOUNDATION, YONSEI UNIVERSITY, Seoul (KR); KOREA ADVANCED INSTITUTE OF SCIENCE AND TECHNOLOGY, Daejeon (KR)

(72) Inventors: Jeong Gil Ko, Yongin-si (KR); Shin Ill Kang, Seoul (KR); In Kyu Park, Daejeon (KR); Jae Yeon Park, Hwaseong-si (KR)

(73) Assignees: INDUSTRY—ACADEMIC COOPERATION FOUNDATION, YONSEI UNIVERSITY, Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 377 days.

(21) Appl. No.: 17/863,397

(22) Filed: Jul. 13, 2022

(65) Prior Publication Data

US 2023/0020419 A1    Jan. 19, 2023

(30) Foreign Application Priority Data

Jul. 16, 2021   (KR) ........................ 10-2021-0093665

(51) Int. Cl.
*A61B 5/00*   (2006.01)
*A61B 5/11*   (2006.01)
(Continued)

(52) U.S. Cl.
CPC ............ *A61B 5/352* (2021.01); *A61B 5/1102* (2013.01); *A61B 5/308* (2021.01)

(58) Field of Classification Search
CPC ....... A61B 5/352; A61B 5/1102; A61B 5/308; A61B 5/7278; A61B 5/327; A61B 5/7246
See application file for complete search history.

(56) References Cited

U.S. PATENT DOCUMENTS 4,736,322 A * 4/1988 Clifford ................. G16H 50/50
482/3
2014/0296722 A1* 10/2014 Schlegel ................ A61B 5/318
600/509

(Continued)

FOREIGN PATENT DOCUMENTS

KR   10-2016-0053718 A   5/2016
KR   10-2020-0084561 A   7/2020

OTHER PUBLICATIONS

Jae Yeon Park et al. 2019. Deep ECG Wave Estimation Model with Seismograph Sensor (poster). 17th Annual International Conference on Mobile Systems, Applications, and Services (MobiSys '19). Association for Computing Machinery, New York, NY, USA, 568-569. https://doi.org/10.1145/3307334.3328629 (Year: 2019).*

(Continued)

*Primary Examiner* — Catherine M Voorhees
*Assistant Examiner* — James Moss

(57) ABSTRACT

An ECG monitoring device includes a vibration meter sensor unit including at least one vibration meter sensor attached to an instrument at which a person to be observed is positioned, and configured to acquire a vibration signal by detecting a vibration transmitted through the instrument in a non-contact or non-invasive method, a filter unit configured to extract a seismocardiography signal ("SCG signal") generated by a heart vibration of the person to be observed by receiving the vibration signal and filtering a predetermined frequency band from the received vibration signal, and an ECG waveform acquisition unit including an artificial neural network learned in advance and configured to generate an (Continued)

electrocardiogram signal ("ECG signal") corresponding to the applied SCG signal according to a learned method.

19 Claims, 9 Drawing Sheets

(51) Int. Cl.
*A61B 5/308* (2021.01)
*A61B 5/352* (2021.01)

(56) References Cited

U.S. PATENT DOCUMENTS

2019/0282178 A1  9/2019  Volosin et al.
2023/0105909 A1* 4/2023  Häscher ............... A61B 5/7253
                                                         600/509

OTHER PUBLICATIONS

Physionet, Combined measurement of ECG, Breathing and Seismocardiograms (CEBS); https://physionet.org/content/cebsdb/1.0.0/, viewed on Jun. 6, 2024 (Year: 2014).*

Steven Smith, The Scientist and Engineer's Guide to Digital Signal Processing, Chapter 14: Introduction to Digital Filters, https://www.dspguide.com/ch14.htm, 2011 (Year: 2011).*

Marian Haescher et al., "Transforming Seismocardiograms Into Electrocardiograms by Applying Convolutional Autoencoders," ICASSP 2020, Barcelona, Spain, 2020, pp. 4122-4126, doi: 10.1109/ICASSP40776.2020.9053130., Published on IEEE Apr. 9, 2020 (Year: 2020).*

Jaeyeon Park et al. 2020. HeartQuake: Accurate Low-Cost Non-Invasive ECG Monitoring Using Bed-Mounted Geophones. Proc. ACM Interact. Mob. Wearable Ubiquitous Technol. 4, 3, Article 93 (Sep. 2020), 28 pages. https://doi.org/10.1145/3411843 (Year: 2020).*

Mathworks. msalign Align peaks in signal to reference peaks. Introduced before R2006a. https://www.mathworks.com/help/bioinfo/ref/msalign.html#FP237668_vh. Viewed on Sep. 21, 2024 (Year: 2006).*

Ghufran Shafiq et al. Automatic Identification of Systolic Time Intervals in Seismocardiogram. Sci Rep. Nov. 22, 2016;6:37524. doi: 10.1038/srep37524. PMID: 27874050; PMCID: PMC5118745. Viewed on Jun. 6, 2024 (Year: 2016).*

\* cited by examiner

NON-INVASIVE TYPE ELECTROCARDIOGRAM MONITORING DEVICE AND METHOD

CROSS REFERENCE TO RELATED APPLICATION

This application claims priority under 35 U.S.C. § 119(a) to Korean Patent Application No. 10-2021-0093665, filed on Jul. 16, 2021, which is hereby incorporated by reference for all purposes as if fully set forth herein.

BACKGROUND

1. Field of the Disclosure

The present disclosure relates to an electrocardiogram (ECG) monitoring device and method, and more particularly, to a non-invasive type ECG monitoring device and method capable of acquiring an accurate ECG waveform using a small vibration meter sensor.

2. Description of the Related Art

In general, heart-related diseases such as arrhythmias and myocardial infarction are diagnosed using an electrocardiogram (hereinafter, referred to as an "ECG") waveform. In order to accurately diagnose heart diseases at an early stage, a continuous ECG waveform analysis rather than short-term fragmentary measurements is required. In particular, cases in which high-risk patients suddenly die from heart-related diseases occur even in large hospitals during the night hours while sleeping in addition to the daytime hours when continuous observation by medical staff is possible.

A Holter test method currently used for monitoring the continuous ECG waveform attaches a plurality of ECG monitoring sensors to the body of a person to be observed and then observes the patient every 24 to 48 hours. However, the Holter test equipment interferes with sleep patterns due to discomfort of wearing, mixing of dynamic noises, or the like because it continuously collects biometric information through the sensors attached to the person to be observed who is sleeping, thereby making it difficult to stably and continuously collect data from the patient to be observed in reality.

In addition, the ECG measuring equipment such as a Holter monitor are very expensive, so that it is difficult to stock a large number of monitors even in large hospitals. Accordingly, it is very difficult for patients who have been discharged from the hospitals or general people who are at risk of heart diseases to use the ECG measuring equipment at home. Accordingly, when a heart is abnormal while sleeping at home, emergency measures may not be taken.

In order to compensate for this problem, a method has been proposed to measure a seismocardiography (hereinafter, referred to as an "SCG") according to the heartbeat of the person to be observed using a sensor and estimate an ECG signal from the measured SCG signal.

As described above, the method of estimating the ECG signal by detecting the vibration has an advantage in that an ECG signal having a certain level of accuracy or more can be acquired even without the ECG measuring equipment, but a vibration signal detected by the vibration sensor includes a lot of noises, and not only a time difference between the ECG and the SCG exists but also the correlation therebetween is not clear, so that there is a limitation to the accuracy of the estimated ECG signal.

SUMMARY

The present disclosure is directed to providing an ECG monitoring device and method capable of accurately estimating an ECG by indirectly detecting an SCG.

The present disclosure is also directed to providing an ECG monitoring device and method capable of estimating a very precise ECG waveform in consideration of a time difference between an SCG and an ECG.

An electrocardiogram (ECG) monitoring device according to one embodiment of the present disclosure includes: a vibration meter sensor unit including at least one vibration meter sensor attached to an instrument at which a person to be observed is positioned and configured to acquire a vibration signal by detecting a vibration transmitted through the instrument in a non-contact or non-invasive method; a filter unit configured to extract a seismocardiography signal (hereinafter, referred to as an "SCG signal") generated by a heart vibration of the person to be observed by receiving the vibration signal and filtering a predetermined frequency band from the received vibration signal; and an ECG waveform acquisition unit including an artificial neural network learned in advance and configured to generate an electrocardiogram signal (hereinafter, referred to as an "ECG signal") corresponding to the applied SCG signal according to a learned method, in which the artificial neural network is learned in advance using a learning SCG signal and a learning ECG signal synchronized so that a peak of the learning SCG signal and an R peak of the learning ECG signal corresponding thereto appear at the same time point in learning data including a plurality of learning SCG signals and a plurality of learning ECG signals corresponding thereto acquired in advance.

The synchronized learning SCG signal and learning ECG signal may be synchronized by acquiring a synchronous time difference by detecting a time point at which the largest correlation value is calculated by cross-correlating the learning SCG signal and the learning ECG signal corresponding thereto while shifting one of the learning SCG signal and the learning ECG signal corresponding thereto in the learning data within a predetermined range on a time axis, and shifting the learning SCG signal or the learning ECG signal corresponding thereto according to the synchronous time difference.

The synchronized learning SCG signal and learning ECG signal may be synchronized by the synchronous time difference acquired according to a time point at which the largest correlation value is calculated by detecting a plurality of peaks of the learning SCG signal and a plurality of R peaks of the learning ECG signal corresponding thereto and performing a cross-correlation at a time point at which positions of the peak of the learning SCG signal and the R peak of the learning ECG signal detected within the predetermined range are matched.

The ECG waveform acquisition unit may acquire the ECG signal having the R peak at the same time point as that of the peak of the SCG signal according to the artificial neural network learned in advance using the synchronized learning SCG signal and learning ECG signal.

The ECG waveform acquisition unit may include: a sampling unit configured to sample the SCG signal at a predetermined sampling rate and convert the sampled SCG signal into SCG data; and an ECG pattern estimation unit implemented as a bidirectional long-short term memory (Bi-LSTM) neural network learned in advance using the synchronized learning SCG signal and learning ECG signal, and configured to estimate a pattern change of the SCG data, which is time-series data, over time and acquire ECG data having a pattern corresponding to the estimated pattern change.

The ECG waveform acquisition unit may further include an ECG waveform analysis unit configured to acquire the ECG signal by receiving the ECG data and converting the received ECG data into an analog signal.

The ECG waveform acquisition unit may additionally extract a plurality of predetermined clinical indicators by analyzing the ECG data.

The filter unit may include: a first filter unit implemented as a low pass filter configured to filter a frequency band exceeding a predetermined first frequency by receiving the vibration signal; and a second filter unit implemented as a high pass filter configured to filter a frequency band lower than a predetermined second frequency by receiving the signal filtered from the first filter unit.

The filter unit may further include a noise analysis unit configured to set the first frequency and the second frequency according to at least one of a noise of the at least one vibration meter sensor itself and a noise generated in a surrounding environment of the instrument, and transmit the set first frequency and second frequency to the first filter unit and the second filter unit.

An ECG monitoring method according to another embodiment of the present disclosure includes: acquiring a vibration signal by detecting a vibration transmitted through an instrument in a non-contact or non-invasive method using at least one vibration meter sensor attached to the instrument at which a person to be observed is positioned; extracting an SCG signal generated by a heart vibration of the person to be observed by receiving the vibration signal and filtering a predetermined frequency band from the received vibration signal; and estimating a pattern of the applied SCG signal and generating an ECG signal of a pattern corresponding to the estimated pattern of the SCG signal using an artificial neural network learned in advance, in which the artificial neural network is learned in advance using a learning SCG signal and a learning ECG signal synchronized so that a peak of the learning SCG signal and an R peak of the learning ECG signal corresponding thereto in learning data including a plurality of learning SCG signals and a plurality of learning ECG signals corresponding thereto acquired in advance appear at the same time point.

Accordingly, an ECG monitoring device and method according to the embodiment of the present disclosure can accurately estimate an ECG signal of a person to be observed by indirectly detecting an SCG using a small vibration meter sensor and allow peaks between an SCG signal and an ECG signal to be acquired as synchronized patterns despite a time difference generated between the SCG and the ECG, thereby performing more precise and accurate ECG analysis.

BRIEF DESCRIPTION OF THE DRAWINGS

The above and other aspects and features of the present disclosure will become more apparent by describing in detail exemplary embodiments thereof with reference to the attached drawings, in which.

DETAILED DESCRIPTION OF THE EMBODIMENTS

Figure 1:
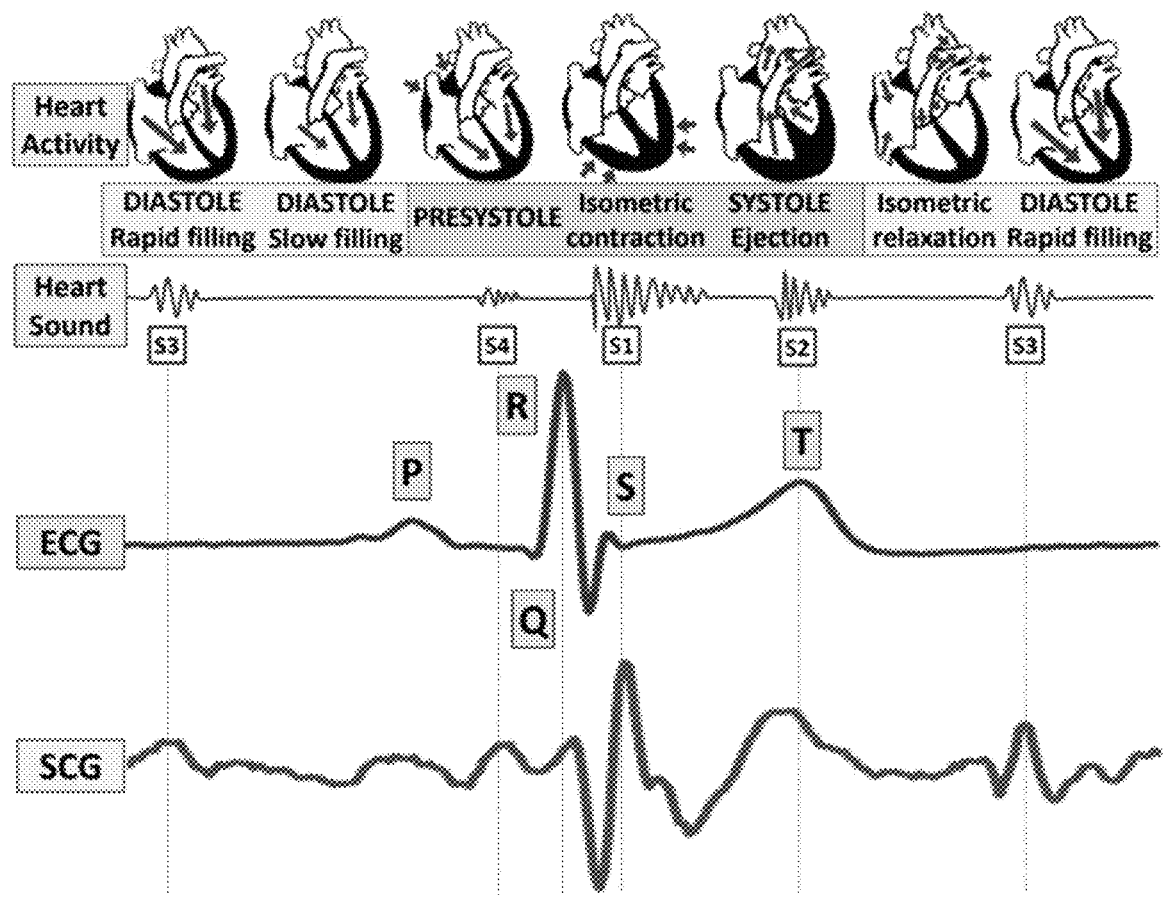
FIG. 1 shows one example of waveforms of ECG and SCG signals according to an operation of a heart.

In order to fully understand the present disclosure, the operational advantages of the present disclosure, and the objects achieved by carrying out the present disclosure, reference should be made to the accompanying drawings showing embodiments of the present disclosure and the contents described in the accompanying drawings.

Hereinafter, the present disclosure will be described in detail by describing the embodiments of the present disclosure with reference to the accompanying drawings. However, the present disclosure may be implemented in various different forms, and is not limited to the described embodiments. In addition, in order to clearly describe the present disclosure, parts irrelevant to the description are omitted, and the same reference numerals in the drawings indicate the same members.

Throughout the specification, when a certain part "includes" a certain component, it means that other components may be further included rather than precluding other components unless specially stated otherwise. In addition, terms such as "... unit", "... machine", "module", "block," and the like described in the specification mean a unit in which at least one function or operation is processed, which may be implemented by hardware or software, and a combination of hardware and software.

FIG. 1 shows one example of waveforms of ECG and SCG signals according to an operation of a heart.

Referring to FIG. 1, a seismocardiography (hereinafter, referred to as an "SCG") signal is a signal detecting a vibration generated in the heart of a person to be observed, and is distinguished from an electrocardiogram (hereinafter, referred to as an ECG) signal that is an electrical signal generated in the heart. Although the SCG signal is also a signal that is useful for analyzing the heart activity of the person to be observed, there is a limitation to accurately understanding the heart activity of the person to be observed only with a pattern of the SCG signal.

However, as shown in FIG. 1, it is well known that there is a high correlation between the waveform of the SCG signal and the waveform of the ECG signal. Both the SCG signal and the ECG signal are time-series signals collected from the human heart, in which the SCG signal represents a vibration due to periodic motion of the heart and blood flow, and the ECG signal represents an electrical signal corresponding to the SCG signal. This is because from a clinical point of view, the electrical activity of the heart causes periodic depolarization and repolarization, resulting in the periodic muscle contraction and relaxation, and blood flow.

In FIG. 1, P, Q, R, S, and T peaks of the ECG signal are generated by the electrical activity of the heart, and four core heart sounds S1 to S4 are also detected from the SCG signal. Specifically, a first heart sound S1 is a closing sound of a mitral valve, which is a valve between a left atrium and a left ventricle, and a second heart sound S2 is a closing sound of an aortic valve, which is a half-moon-shaped valve connecting ventricles. In addition, a third heart sound S3 is an exogenous sound caused by rapid filling of the aorta, and a fourth heart sound S4 is a gallop rhythm of the entire process of arterial contraction, and all of the heart sounds are generated by the electrical activity of the heart.

Accordingly, when the SCG signal and the ECG signal are measured together, as shown in FIG. 1, it has a pattern in which the peak of the ECG signal appears temporally earlier, and then the peak of the SCG signal appears delayed according to the heart activity by the ECG signal.

However, due to the diversity of the pattern of the SCG signal and the complexity of noise, the relationship between the pattern of the SCG signal and the pattern of the ECG signal has not yet been accurately found. Accordingly, conventionally, even when the SCG signal is acquired, the ECG signal should be separately monitored.

However, in the present disclosure, the ECG signal is extracted from the SCG signal using an artificial neural network learned in advance. In particular, in the present disclosure, it is possible to extract an ECG signal with very high accuracy by using the artificial neural network learned in consideration of a time difference between the SCG signal and the ECG signal.

Figure 2:
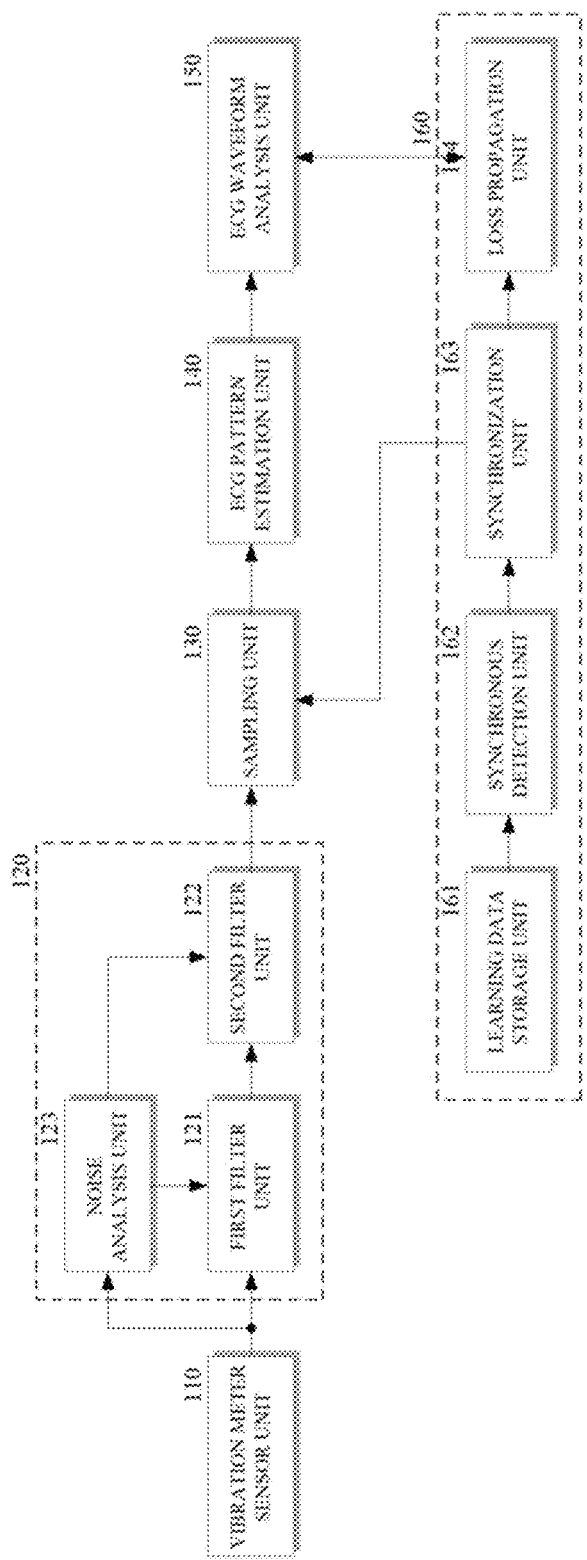
FIG. 2 shows a schematic structure of an ECG monitoring device according to one embodiment of the present disclosure.
Figure 3:
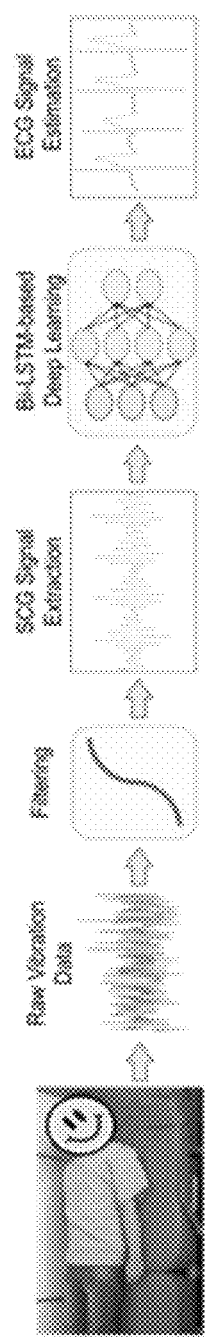
FIG. 3 is a view for describing an operation of each component of the monitoring device in FIG. 2.

FIG. 2 shows a schematic structure of an ECG monitoring device according to one embodiment of the present disclosure, and FIG. 3 is a view for describing the operation of each component of the monitoring device in FIG. 2.

Referring to FIG. 2, the ECG monitoring device according to this embodiment includes a vibration meter sensor unit 110, a filter unit 120, a sampling unit 130, an ECG pattern estimation unit 140, and an ECG waveform analysis unit 150.

The vibration meter sensor unit 110 is implemented as a small vibration sensor and detects vibrations generated by a person to be observed. In this embodiment, the vibration meter sensor unit 110 may be implemented as, for example, a geophone, which is a small vibration meter sensor. The geophone may be configured to include a coil, a magnet, and two springs disposed at upper and lower ends to measure the amount of vibration from an inertial mass applied to the spring. In particular, here, the geophone is widely used to detect earthquakes in the surrounding environment, and a small and low-cost SM-24 geophone sensor may be used. The SM-24 geophone sensor may provide a reliable sensitivity of 28.8 V/m/s in a frequency range of 0.5 to 50 Hz at low cost. In addition, the vibration meter sensor unit 110 does not need to come into direct contact with the body of the person to be observed, unlike the conventional ECG measuring equipment.

As described above, the human heart repeats contraction and relaxation actions in a process of supplying blood, and in this process, a minute SCG is generated. It is difficult for conventional vibration sensors to detect weak vibrations such as the SCG of the person to be observed who does not come into direct contact therewith, but recently, the small vibration meter sensor such as the geophone may have an improved sensitivity, so that it is possible to detect the SCG of the person to be observed only by coming into indirect contact therewith without coming into direct contact with the person to be observed.

Accordingly, in this embodiment, the vibration meter sensor unit 110 is attached to various furniture such as a bed, a chair, and the like on which the person to be observed is positioned to detect vibrations only by coming into indirect contact with the person to be observed. A position at which the vibration meter sensor unit 110 is disposed is not limited, but in this embodiment, for example, as shown in FIG. 3, it is assumed that the vibration meter sensor unit 110 is installed on the bed on which the person to be observed lies. The vibration meter sensor unit 110 may be, for example, disposed on an upper panel of a mattress to effectively detect the heart vibration of the person to be observed. In particular, the vibration meter sensor unit 110 may be disposed on the upper panel of a left shoulder of the person to be observed. Accordingly, the ECG monitoring device according to this embodiment may easily detect the SCG of the person to be observed who is sleeping.

The vibration meter sensor unit 110 may transmit a vibration signal corresponding to the detected vibration to the filter unit 120 in a wired or wireless manner.

The filter unit 120 acquires the SCG signal by filtering and removing noise included in the vibration signal applied from the vibration meter sensor unit 110. The vibration signal acquired from the vibration meter sensor unit 110 includes various noises as well as vibrations generated in the heart of the person to be observed. Even when the vibration meter sensor unit 110 comes into direct contact with the person to be observed, the vibration meter sensor unit 110 may detect various vibrations such as vibrations due to the respiration, blood flow, and movement of the person to be observed together with the heart vibration of the person to be observed, and various vibrations may be included as noises. In particular, in this embodiment, the vibration meter sensor unit 110 comes into indirect contact with the person to be observed to detect vibrations without coming into direct contact with or invading the person to be observed. Accordingly, the indirect contact method may further include various noises caused by the surrounding environment than the direct contact method. In addition, in some cases, an inertial noise of the vibration sensor itself or the like may also be included.

Accordingly, the filter unit 120 acquires the SCG signal by filtering and removing the remaining noise components other than the heart vibration component from the vibration signal applied from the vibration meter sensor unit 110.

The filter unit 120 may be configured to receive the vibration signal from the vibration meter sensor unit 110, pass through only a signal of a predetermined frequency band from the received vibration signal, and block a remaining signal of the frequency band, thereby removing the noise included in the vibration signal.

Figure 4A:
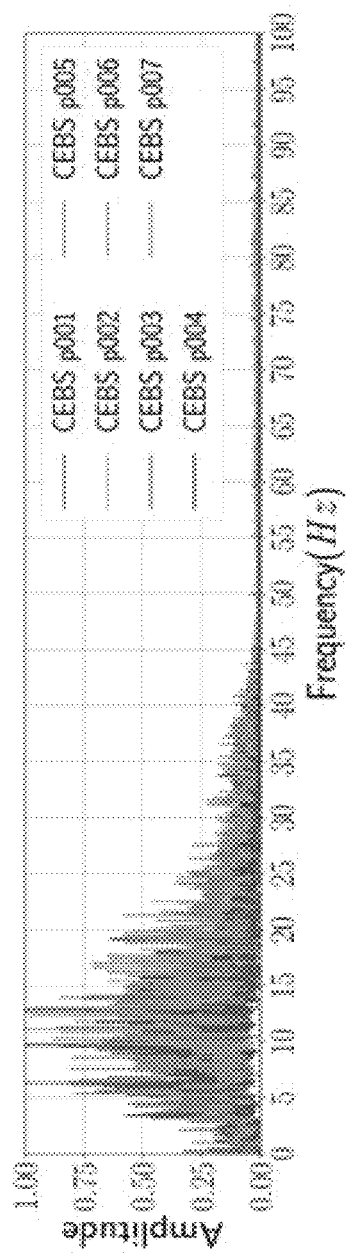
FIGS. 4A and 4B show a frequency distribution of an SCG signal waveform measured from a plurality of persons to be observed.
Figure 4B:
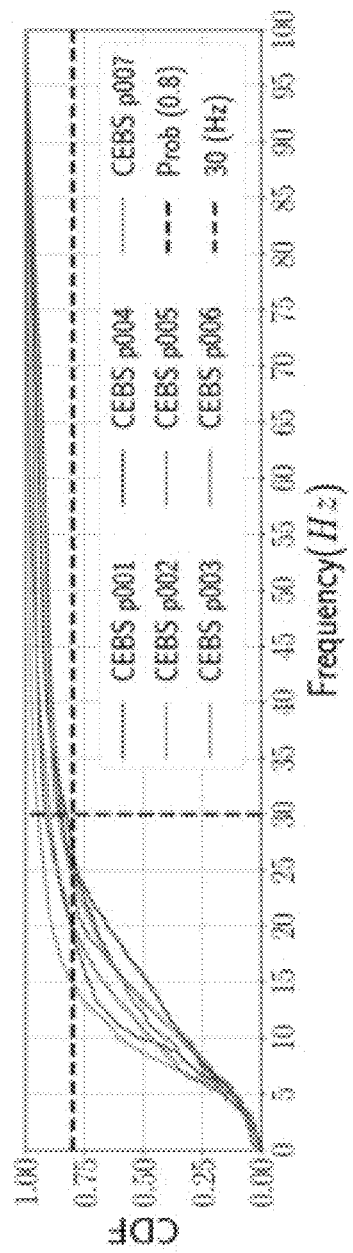

FIGS. 4A and 4B show a frequency distribution of an SCG signal waveform measured from a plurality of persons to be observed.

FIGS. 4A and 4B show a result of measuring the SCG signals for a plurality of persons to be observed, wherein FIG. 4A shows a frequency signal of the SCG signal obtained by Fast Fourier Transformation for the SCG signal measured using the conventional measuring equipment, and FIG. 4B shows a cumulative distribution according to the frequency for the frequency signal of FIG. 4A. As shown in FIGS. 4A and 4B, it may be seen that the SCG signal includes most of the signal components in a frequency band of 0 to 45 Hz regardless of the person to be observed. In addition, even when the SCG signal is acquired using the measuring equipment, noises such as the breathing of the person to be observed are included, so that a signal component in a band of 5 Hz or less is generally treated as noise.

Accordingly, the filter unit 120 may be implemented as a band pass filter (BPF) configured to leave only a signal component in a frequency band of 5 to 45 Hz from the received vibration signal and block the remaining signal components.

However, since the band pass filter performs filtering so that both frequency bands are symmetric with respect to a center frequency fc, filtering is not easy when noises are asymmetrically distributed in several frequency bands. Accordingly, in this embodiment, the filter unit 120 may be configured to filter noises by combining a low pass filter and a high pass filter, and thus may include a first filter unit 121 implemented as a low pass filter (LPF) and a second filter unit 122 implemented as a high pass filter (HPF).

In the filter unit 120, in order to pass through only the signal in the frequency band of 5 to 45 Hz, a cutoff frequency Gut of the first filter unit 121 may be set to 45 Hz, and a cutoff frequency $f_{cut}$ of the second filter unit 122 may be set to 5 Hz.

However, in the ECG monitoring device according to this embodiment, since the vibration meter sensor unit 110 detects the person to be observed in an indirect contact method, the vibration due to the surrounding environment may be detected together and included as noise, and in addition, since the vibration meter sensor unit 110 is used by replacing the ECG measuring device, the inertial noise may be detected together in the vibration meter sensor itself configuring the vibration meter sensor unit 110. Accordingly, the filter unit 120 may be implemented to change a filtering frequency to adaptively remove the noise generated by the vibration meter sensor itself and various noises generated by the surrounding environment.

Accordingly, in this embodiment, the filter unit 120 may further include a noise analysis unit 123 configured to set a frequency band to be filtered by the filter unit 120 to perform an adaptive filtering.

The noise analysis unit 123 may first measure and store a frequency component of the noise of the vibration meter sensor itself configuring the vibration meter sensor unit 110 in advance. For example, when the vibration meter sensor is an SM-24 geophone sensor, it is known that a lot of noises occur in a frequency band of 0 to 5 Hz, and a high peak noise occurs around a frequency of 30 Hz. In addition, as shown in FIGS. 4A and 4B, although the SCG signal is distributed in a frequency band of 5 to 45 Hz, a signal component of about 80% or more is included in a frequency band of 5 to 30 Hz. Accordingly, the noise analysis unit 123 may control the first and second filter units 121 and 122 to filter a frequency band lower than 5 Hz and a frequency band exceeding 30 Hz in order to acquire the SCG signal while removing the noise of the vibration meter sensor itself from the vibration signal.

When another vibration meter sensor is used, the noise analysis unit 123 may store the frequency of the inherent noise in the used vibration meter sensor to control the first and second filter units 121 and 122 to filter the corresponding frequency.

In addition, the noise analysis unit 123 may analyze and store the frequency component of the noise generated by the surrounding environment in advance from the signal detected while the person to be observed is not positioned on an instrument such as a bed or a sofa to which the vibration meter sensor unit 110 is attached. For example, the noise analysis unit 123 may analyze the surrounding environmental noise when a signal of a specific frequency band is not included in the vibration signal acquired in a predetermined time zone or the received vibration signal. Here, the noise analysis unit 123 may analyze the surrounding environmental noise by analyzing the vibration signal applied in the morning or during the daytime when the person to be observed is not in a sleep state. In a state in which the person to be observed is not positioned on the bed to which the vibration meter sensor unit 110 is attached, the noise analysis unit 123 may store the vibration signal in a frequency band of 5 to 35 Hz detected as a predetermined reference intensity or less as the surrounding environmental noise, and then subtract the stored vibration signal according to the surrounding environmental noise from the vibration signal in the frequency band of 5 to 35 Hz to acquire the accurate SCG signal with the surrounding environmental noise removed when the SCG signal is acquired.

As shown in FIG. 3, when the filter unit 120 filters the vibration signal to acquire the SCG signal, the sampling unit 130 receives and samples the acquired SCG signal, and digitally converts the sampled SCG signal, so that SCG data may be acquired. The sampling unit 130 may sample the SCG signal at a sampling rate of a predetermined frequency (e.g., 250 Hz) higher than the filtering frequency of the filter unit 120, so that the SCG data may be acquired. At this point, the sampling unit 130 may normalize the sampled SCG data to a predetermined range (here, for example, [−1:1]).

The ECG pattern estimation unit 140 acquires ECG data from the SCG data.

As shown in FIG. 3, the ECG pattern estimation unit 140 is implemented as an artificial neural network learned in advance and acquires the ECG data from the digitally converted SCG data. The ECG pattern estimation unit 140 may be implemented as various artificial neural networks, but for example, may be implemented as a bidirectional long short-term memory (LSTM) (hereinafter, referred to as a "Bi-LSTM").

The Bi-LSTM is configured to include a forward layer including a plurality of LSTM cells configured to transmit and process information in a forward direction based on a time, and a backward layer including the plurality of LSTM cells configured to transmit and process information in a backward direction based on the time, so that it is possible to easily extract ECG patterns that appear differently depending on each of the persons to be observed.

Figure 5:
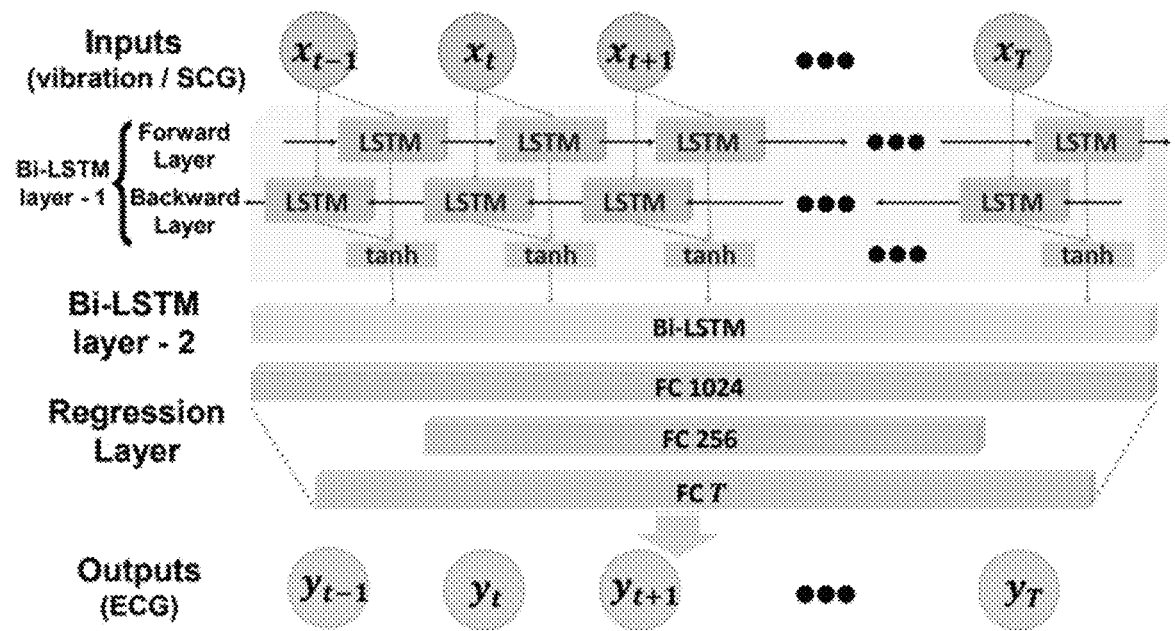
FIG. 5 shows one example of a detailed configuration of an ECG pattern estimation unit in FIG. 1.

FIG. 5 shows an example of a detailed configuration of the ECG pattern estimation unit in FIG. 2.

Referring to FIG. 5, in this embodiment, the ECG pattern estimation unit 140 may include two Bi-LSTM layers (Bi-LSTM layer-1 and Bi-LSTM layer-2) and a regression layer, and each of the two Bi-LSTM layers (Bi-LSTM layer-1 and Bi-LSTM layer-2) may include the forward layer and backward layer including the plurality of LSTM cells, and an activation layer.

When the ECG pattern estimation unit 140 uses an LSTM layer including only the forward layer other than the Bi-LSTM layer, an initial sequence $x_{t-1}$ may be processed as relatively less important than a late sequence $x_T$ applied later in the SCG signal while the applied SCG signal passes through the plurality of LSTM cells of the LSTM layer. On the other hand, since the Bi-LSTM layer includes both the forward layer and the backward layer, forward sequences ($x_{t-1}$, $x_t$, $x_{t+1}$, . . . $x_T$) and backward sequences ($x_T$, $x_{T-1}$, . . . $x_{t-1}$) may be temporally processed equally in the SCG signal. In other words, the Bi-LSTM layer allows both regions to temporally have equal importance in the applied SCG signal.

In addition, the activation layer may be implemented as a hyperbolic tangent function (tanh) so that the outputs of the two Bi-LSTM layers are normalized to the predetermined range (here, for example, [−1:1]) and output like the input SCG data.

The ECG pattern estimation unit 140 extracts the SCG data in the corresponding region while moving a sliding window in chronological order with respect to the SCG data transmitted from the sampling unit 130 and transmits the SCG data to each of the forward layer and backward layer of the first Bi-LSTM layer (Bi-LSTM layer-1) of the two Bi-LSTM layers (Bi-LSTM layer-1 and Bi-LSTM layer-2).

At this point, the size of the sliding window may be set to the size of two or more periods of the SCG signal. This is to allow the SCG data corresponding to two periods in the SCG signal to be simultaneously applied to the first Bi-LSTM layer (Bi-LSTM layer-1) so that the relationship between the pattern of the SCG signal and the pattern of the ECG signal according to the ECG data may be accurately estimated. In particular, in order to accurately estimate the time relationship between two continuous periods of the ECG signal like an RR interval representing an interval between the R peaks shown in FIG. 1 as one of the critical indicators in the ECG signal, the size of the sliding window may be set to the size of two or more periods of the SCG signal.

Accordingly, in this embodiment, it is assumed that the size of the sliding window is set to the size including the SCG data corresponding to two or more times (here, for example, three times) a length of a specified sampling rate.

In addition, the ECG pattern estimation unit 140 is provided with the two Bi-LSTM layers (Bi-LSTM layer-1 and Bi-LSTM layer-2), and the second Bi-LSTM layer (Bi-LSTM layer-2) receives the output of the first Bi-LSTM layer (Bi-LSTM layer-1) in order to accurately map the nonlinear relationship between the SCG signals and the ECG signals of various patterns. In particular, this is to reflect the relationship between the SCG data extracted from the previous sliding window and the SCG data extracted from the next sliding window.

In other words, since the two Bi-LSTM layers (Bi-LSTM layer-1 and Bi-LSTM layer-2) are disposed in a stacked structure, the ECG pattern estimation unit 140 can clearly estimate the change pattern relationship of the heart rate signal in a wide time segment.

The ECG data at a specific time point T may be acquired by classifying the characteristics of the SCG data extracted through the first and second Bi-LSTM layers (Bi-LSTM layer-1 and Bi-LSTM layer-2) including a plurality of fully connected layers FC of the regression layer. Since the sliding window extracts and transmits SCG data of a specified size from the SCG data continuously applied over time, the regression layer may continuously acquire the ECG data according to each time point. At this point, the plurality of fully connected layers FC may be connected in series to have a structure in which the size is gradually reduced, and may be finally configured to output the ECG data at the specific time point T.

The ECG pattern estimation unit 140 may be learned using a plurality of learning data including the SCG data and ECG data measured using separate measuring equipment or the like. The ECG pattern estimation unit 140 receives the SCG data acquired by measuring the learning data in advance as an input and outputs the ECG data estimated from the received SCG data. When the ECG data is output, by repeating a process of calculating an error between the output ECG data and the ECG data corresponding to the input SCG data among the learning data and propagating the calculated error back to the ECG pattern estimation unit 140 so that the error is a predetermined reference error or less, the ECG pattern estimation unit 140 implemented as the artificial neural network may be learned.

In other words, the ECG pattern estimation unit 140 is learned using the SCG data and the ECG data of the learning data, and thus as shown in FIG. 3, may output the ECG data corresponding to the SCG data applied from the sampling unit 130.

This is a supervised learning method, which is a general learning method for the artificial neural network and exhibits excellent performance in many cases.

Figure 6A:
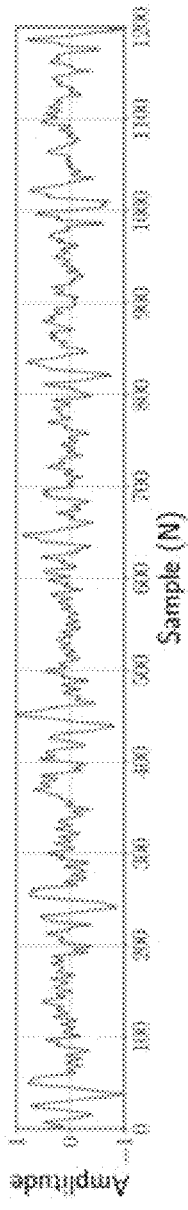
FIGS. 6A-6C show waveforms of a vibration signal acquired by a vibration meter sensor unit, a SCG signal filtered by a filter unit, and an ECG signal extracted by an ECG pattern estimation unit in FIG. 1.
Figure 6B:
Figure 6C:
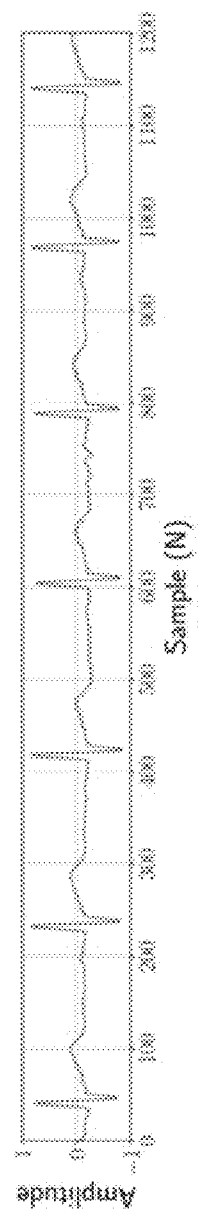

FIGS. 6A-6C shows waveforms of a vibration signal acquired by a vibration meter sensor unit, an SCG signal filtered by a filter unit, and an ECG signal extracted by an ECG pattern estimation unit in FIG. 1.

In FIGS. 6A-6C, FIG. 6A shows the vibration signal acquired by the vibration meter sensor unit 110, FIG. 6B shows the SCG signal filtered by the filter unit 120, and FIG. 6C shows the ECG signal according to the ECG data extracted by the ECG pattern estimation unit 140 learned according to the general supervised learning method.

As shown in FIG. 6A, the vibration signal acquired from the vibration meter sensor unit 110 includes a plurality of noises, but it may be seen that the noise is removed by the filter unit 120 from the SCG signal of FIG. 6B, so that the pattern of the waveform is clearer. In addition, it may be seen that the ECG signal in FIG. 6C extracted from the SCG signal has been extracted as a very regular waveform to estimate the heart condition of the person to be observed. In other words, it may be seen that the ECG signal has been acquired at a level at which the medical staff may roughly determine the heart condition of the person to be observed.

The ECG waveform analysis unit 150 may acquire the ECG signal from the ECG data acquired by the ECG pattern estimation unit 140. The ECG waveform analysis unit 150 may acquire the ECG signal by converting the ECG data into an analog signal. In addition, the ECG waveform analysis unit 150 may extract a plurality of clinically critical indicators from the acquired ECG signal.

Figure 7:
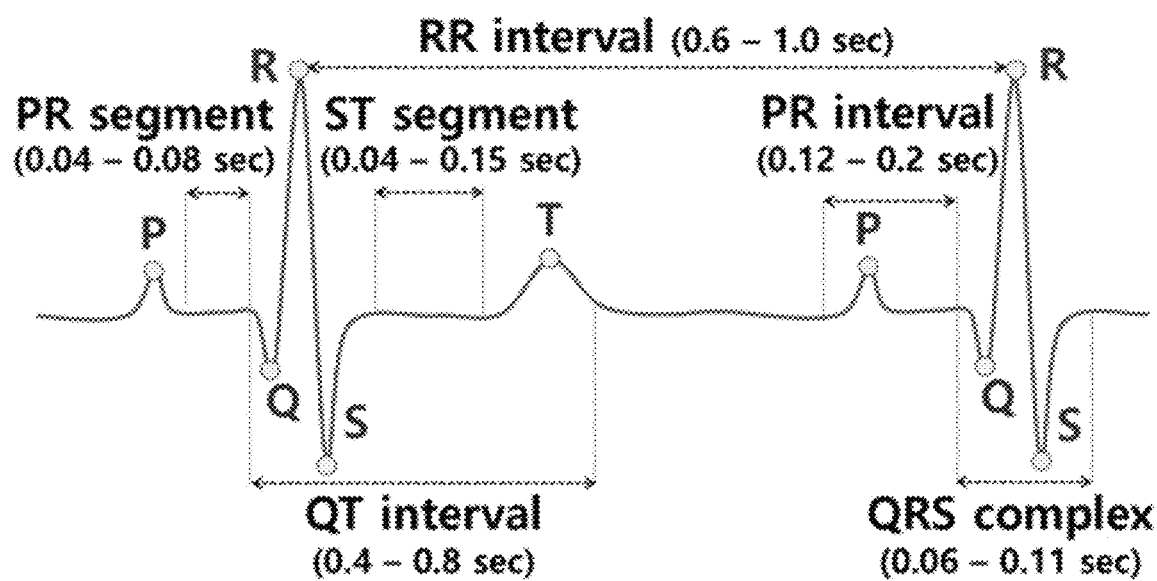
FIG. 7 is a view for describing critical clinical indicators according to the waveform of the ECG signal.

FIG. 7 is a view for describing critical clinical indicators according to the waveform of the ECG signal.

As shown in FIG. 7, the ECG waveform analysis unit 150 may extract and output various clinical indicators (e.g., time stamps such as P, Q, R, S, T, RR interval, and QRS segment length) including five peaks (P, Q, R, S, and T) from the ECG signal.

Figure 8A:
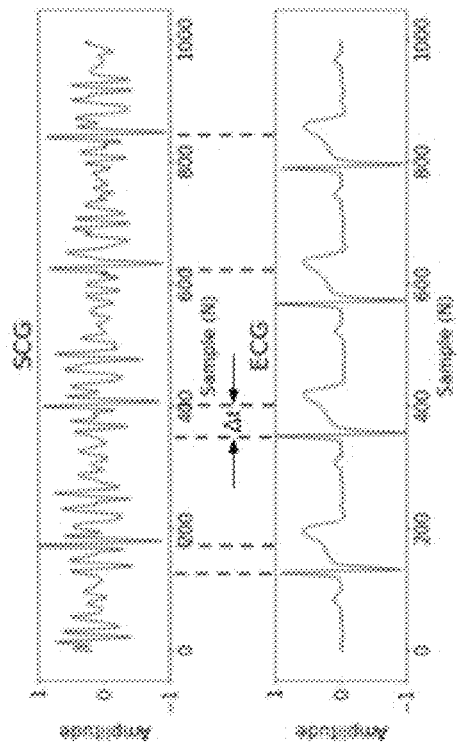
FIGS. 8A and 8B are a view for describing an operation of a synchronous preprocessing unit.
Figure 8B:
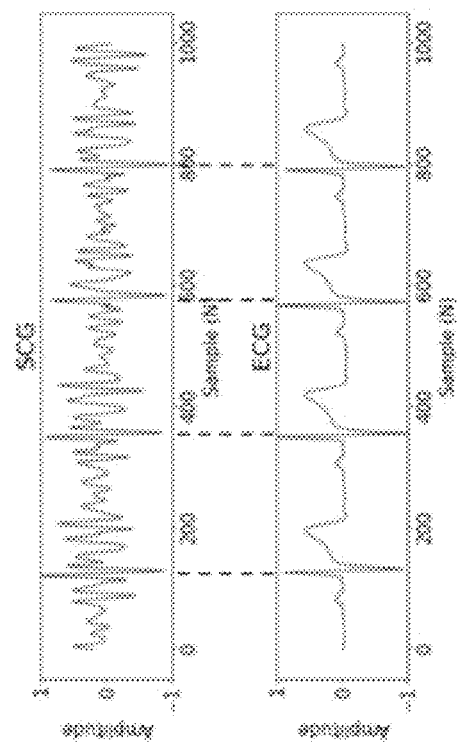

Here, the time stamps such as the RR interval and the QRS segment length mean a time segment according to five peaks (P, Q, R, S, and T) of the ECG waveform, as shown in FIGS. 8A and 8B. FIG. 7 shows the time stamps for normal people without heart diseases together.

Here, the ECG waveform analysis unit 150 extracts a plurality of predetermined clinical indicators in order to easily determine the heart condition from the ECG data, and may also be omitted in some cases. In addition, although it has been described above that the ECG waveform analysis unit 150 analog-converts the ECG data into the ECG signal and extracts the clinical indicators, the ECG waveform analysis unit 150 may also be configured to directly extract the clinical indicators from the ECG data.

As described above, the ECG monitoring device in FIG. 1 may acquire the ECG signal at the level at which the heart condition of the person to be observed may be roughly determined even when the ECG pattern estimation unit 140 implemented as the artificial neural network is learned according to the general supervised learning method.

However, in some cases, a more precise and accurate ECG signal may be required to accurately analyze the condition of the person to be observed. In particular, when the person to be observed has the heart disease, the ECG signal with high accuracy is necessarily required to accurately analyze the condition of the person to be observed.

However, the patterns of the SCG signal and the ECG signal varies from person to person. In addition, as shown in FIG. 1, a time difference (also referred to as a "phase difference") basically exists between the SCG signal and the ECG signal, and both the SCG signal and the ECG signal appear as patterns repeated according to the heartbeat. However, even in the SCG signal and the ECG signal for the same person to be observed, the patterns or repetition periods thereof are frequently changed depending on the condition of the person to be observed. In addition, since the vibration meter sensor configured to measure the SCG signal, the Holter monitor configured to measure the ECG signal, and the like are individually operated when the learning data is acquired, the time difference variously appears due to various factors such as the measurement time difference of each measuring equipment and the operation speed of the equipment itself. This means that noises and separate unnecessary error factors between the SCG signal and the ECG signal acquired for learning are further included, which is an obstacle to acquiring the accurate ECG signal. In addition, when the time difference between the SCG signal and the ECG signal is half the heartbeat cycle or more, the ECG monitoring device may acquire the ECG signal or a distorted ECG signal according to the SCG signal at a wrong timing.

Accordingly, the ECG monitoring device according to this embodiment may further include a synchronous learning unit 160 configured to learn the ECG pattern estimation unit 140. In this embodiment, the synchronous learning unit 160 compensates for the time difference between the SCG signal and the ECG signal included in the learning data when the ECG pattern estimation unit 140 is learned, to perform learning, so that the ECG pattern estimation unit 140 may allow more accurate ECG data to be acquired from the SCG data. The synchronous learning unit 160 may be provided only when the monitoring device is learned and removed after the learning is completed.

The synchronous learning unit 160 may include a learning data storage unit 161, a synchronous detection unit 162, a synchronization unit 163, and a loss propagation unit 164.

The learning data storage unit 161 stores a plurality of SCG signals acquired by measuring a plurality of persons to be observed in advance and a plurality of ECG signals corresponding thereto. Hereinafter, the SCG signal and the ECG signal acquired in advance for learning are referred to as a learning SCG signal and a learning ECG signal, respectively.

The synchronous detection unit 162 detects a synchronization time by receiving the learning SCG signal and the learning ECG signal corresponding thereto stored in the learning data storage unit 161 and cross-correlating between the received learning SCG signal and learning ECG signal. The synchronous detection unit 162 may acquire a synchronous time difference $\Delta t$ by cross-correlating the learning SCG signal and the learning ECG signal while shifting one of the received learning SCG signal and learning ECG signal along a time axis and detecting a time point at which the highest correlation value is detected as a synchronous time point. In this case, the synchronous detection unit 162 may detect a time point at which the peak of the learning SCG signal and the R peak of the learning ECG signal match with each other as the synchronous time point. Here, for example, it will be described by assuming that the learning ECG signal cross-correlates with the learning SCG signal while being shifted.

In general, since the SCG signal should be detected after the ECG signal, the learning ECG signal basically cross-correlates with the learning SCG signal while being delayed. However, as described above, in the present disclosure, there often occurs a case in which a phase of the learning SCG signal is earlier than a phase of the learning ECG signal in the acquired learning data due to the delay caused by detecting the SCG signal through the indirect vibration and a difference in performance of the measuring equipment configured to measure the SCG signal and the ECG signal. Accordingly, the synchronous detection unit 162 may detect the synchronous time point by performing the cross-correlation with the remaining signal while advancing or delaying one of the learning SCG signal and the learning ECG signal within a predetermined segment on the time axis.

At this point, there may be many time points at which the correlation value has a peak greater than or equal to a reference value due to the characteristics of the ECG signal and the SCG signal having the repeated patterns, but the synchronous time difference $\Delta t$ may be acquired by determining that the correlation value between the learning ECG signal and the learning SCG signal corresponding to each other is the largest and setting the time point with the largest correlation value as the synchronous time point. However, even when the cross-correlation between the learning ECG signal and the learning SCG signal is performed, positions calculated as having the high correlation value are eventually the R peak of the ECG signal and the peak of the SCG signal repeated in similar patterns. Accordingly, it is very inefficient to perform the cross-correlation operation for the entire region in the specified range segment. In addition, as shown in FIG. 1, in the state in which the learning ECG signal and the learning SCG signal are acquired, the positions of the peaks of the learning ECG signal and the learning SCG signal may be identified in advance. Accordingly, the synchronous detection unit 162 calculates the correlation value by identifying the positions of the peaks of the learning ECG signal and the learning SCG signal corresponding to each other in the learning data in advance and cross-correlating the learning ECG signal and the learning SCG signal only at the identified positions of the peaks, so that it is possible to significantly reduce the amount of operations for acquiring the synchronous time difference $\Delta t$. In other words, the synchronous time difference $\Delta t$ may be acquired by comparing the correlation values calculated at each peak to detect the time difference up to the time point appearing as the highest correlation value as the synchronous time difference $\Delta t$.

The synchronization unit 163 synchronizes the learning ECG signal and the learning SCG signal so that the time points of the peaks of the learning ECG signal and the learning SCG signal corresponding to each other are matched by shifting one of the learning ECG signal and the learning SCG signal according to the synchronous time difference $\Delta t$ acquired by the synchronous detection unit 162. In addition, the synchronization unit 163 transmits the learning SCG signal synchronized with the learning ECG signal to the sampling unit 130 when the ECG pattern estimation unit 140 of the ECG monitoring device is learned, whereas the learning ECG signal corresponding thereto is transmitted to the loss propagation unit 164.

Here, the synchronous detection unit 162 and the synchronization unit 163 may be referred to as synchronous preprocessing units configured to perform a synchronous preprocessing of the learning data.

FIGS. 8A and 8B are a view for describing an operation of a synchronous preprocessing unit.

As shown in FIG. 8A, the synchronous detection unit 162 in the synchronous preprocessing unit acquires the synchronous time difference Δt by receiving the learning ECG signal and the learning SCG signal whose peaks appear at different times on the time axis and detecting the time difference between the peaks of the learning ECG signal and the learning SCG signal. In addition, the synchronization unit 163 shifts one of the learning ECG signal and the learning SCG signal on the time axis by the synchronous time difference Δt, so that as shown in FIG. 8B, the learning ECG signal or the learning SCG signal is synchronized and output to match the time points at which the peaks of the learning SCG signal and the learning ECG signal are generated.

When the sampling unit 130 acquires the learning SCG data by receiving and sampling the learning SCG signal synchronized from the synchronization unit 163, the ECG pattern estimation unit 140 estimates the ECG data according to the method learned until that point from the learning SCG data, and the ECG waveform analysis unit 150 acquires the ECG signal by converting the ECG data into the analog signal, the loss propagation unit 164 calculates an error in a predetermined method between the ECG signal acquired from the ECG waveform analysis unit 150 and the learning ECG signal transmitted from the synchronization unit 163 and calculates the error as the loss of the ECG pattern estimation unit 140, which is the artificial neural network, to propagate the calculated error back, so that the ECG pattern estimation unit 140 is learned.

As described above, in this embodiment, by learning the ECG pattern estimation unit 140 using the synchronized learning ECG signal and learning SCG signal after synchronizing the learning ECG signal and the learning SCG signal of the learning data in advance, the ECG monitoring device may extract the ECG signal with a more accurate and precise pattern from the SCG signal later.

In addition, as described above, since the ECG monitoring device is learned to estimate and output the learning ECG signal synchronized with the learning SCG signal, the SCG signal is output necessarily later than the ECG signal in reality, but the ECG monitoring device according to this embodiment may acquire and output the ECG signal, which causes the generation of the SCG signal, as the synchronized waveform at the same time point as in FIG. 8B. In other words, it is possible to improve the convenience of the analyses of the SCG signal and the ECG signal by enabling an observer to easily identify the waveforms of the SCG signal and the ECG signal corresponding to each other as well as enabling a more accurate ECG signal to be generated.

Figure 9:
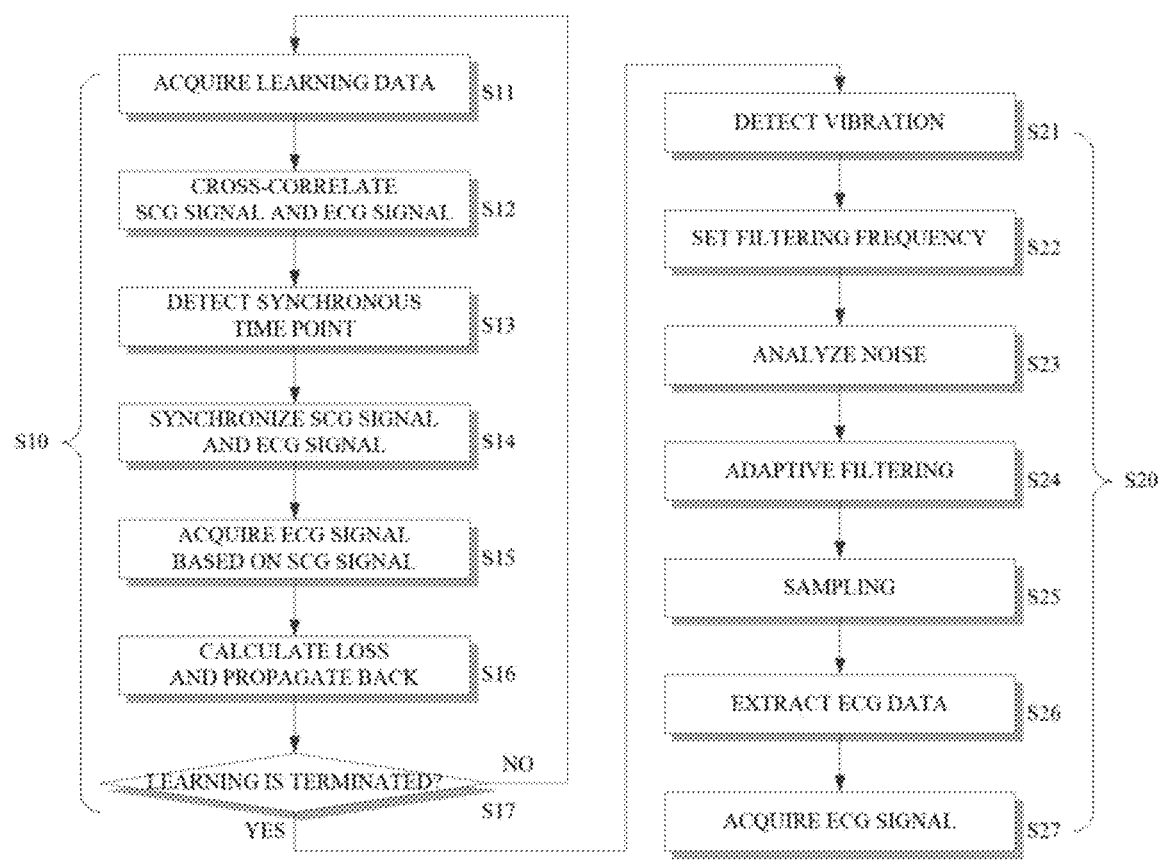
FIG. 9 shows an ECG monitoring method according to one embodiment of the present disclosure.

FIG. 9 shows an ECG monitoring method according to one embodiment of the present disclosure.

Describing the ECG monitoring method in FIG. 9 with reference to FIGS. 1 to 8, first, learning for learning an ECG pattern estimation unit 140 implemented as an artificial neural network is performed (S10).

In the learning operation (S10), first, an SCG signal to be learned and an ECG signal corresponding thereto among learning data including a plurality of learning SCG signals and a plurality of learning ECG signals corresponding thereto are acquired (S11). Here, the plurality of learning SCG signals and the plurality of learning ECG signals may be acquired in advance using equipment such as a vibration meter sensor and a Holter monitor, respectively.

When the learning SCG signal and the learning ECG signal corresponding thereto are acquired, a correlation value is calculated by moving one of the acquired learning SCG signal and learning ECG signal corresponding thereto in positive and negative directions within a predetermined range on the time axis and cross-correlating the SCG and ECG signals (S12). At this point, it is also possible to increase operation efficiency by detecting positions of a plurality of peaks of the learning SCG signal and positions of a plurality of R peaks of the learning ECG signal without moving the learning SCG signal or the learning ECG signal in all regions within the range, and then identifying time points at which the plurality of peaks of the learning SCG signal and the plurality of R peaks of the learning ECG signal are matched, and calculating the correlation values of only the corresponding positions.

In addition, the time point having the highest correlation value among the calculated correlation values is detected as a synchronous time point, and a synchronous time difference Δt is acquired according to the detected synchronous time point (S13). When the synchronous time point Δt is acquired, the learning SCG signal and the learning ECG signal are synchronized by moving one of the learning SCG signal and the learning ECG signal on the time axis according to the acquired synchronous time difference Δt (S14).

When the learning SCG signal and the learning ECG signal are synchronized, the learning SCG data is acquired by transmitting and sampling the learning SCG signal to a sampling unit 130, and the ECG pattern estimation unit 140 estimates ECG data according to a method learned until that point from the learning SCG data, and the ECG waveform analysis unit 150 converts the ECG data into an analog signal, so that the ECG signal is acquired (S15).

When the ECG signal is acquired corresponding to the learning SCG signal, the ECG pattern estimation unit 140 is learned by calculating an error between the acquired ECG signal and the learning ECG signal corresponding to the learning SCG signal as a loss and propagating the calculated loss back to the ECG pattern estimation unit 140 (S16).

In addition, it is determined whether the learning is terminated (S17). Here, the termination of learning may be set to a case in which the number of learning times repeatedly performed reaches the number of predetermined reference times. However, the learning may also be set to be terminated when the calculated loss is smaller than or equal to a predetermined reference loss.

When it is determined that the learning is required to be continuously performed because the condition in which learning is to be terminated is not satisfied, the learning is repeated by acquiring the learning SCG signal to be learned again and the learning ECG signal corresponding thereto (S11).

On the other hand, when it is determined that the learning has been terminated, a vibration signal is acquired by detecting vibration through at least one vibration sensor attached to an instrument at which a person to be observed is positioned without coming into contact with or invading the person to be observed (S21). At this point, the acquired vibration signal may include the vibrations caused by breathing, movement, or the like of the person to be observed along with the heart vibration of the person to be observed, and the noises due to the vibrating meter sensor itself and the surrounding environment.

In addition, while the person to be observed is not positioned on the instrument, a filtering frequency for removing the noise by analyzing the previously acquired vibration signal is set (S22). Here, the noise may include the noise of the vibration meter sensor itself and the noise due to the surrounding environment, and the noise of the vibration meter sensor itself may be directly input and stored in the form of a user command. However, a minimum frequency band capable of maintaining the SCG signal component may be set in advance so that the SCG signal component included in the vibration signal is not significantly damaged by the set filtering frequency, and in some cases, the minimum frequency band for the SCG signal may also be set to the filtering frequency without analyzing the noise.

When the filtering frequency is set, the SCG signal is acquired by filtering the vibration signal according to the set filtering frequency (S24). Here, the noise filtering may be performed by a combination of a low pass filter and a high pass filter. In addition, the SCG data is acquired by sampling the acquired SCG signal at a predetermined sampling rate and digitally converting the sampled SCG signal (S25).

Meanwhile, when the SCG signal is acquired, the ECG data is extracted by estimating the pattern of the SCG signal using the artificial neural network learned in advance in the learning operation (S10) (S25). At this point, a Bi-LSTM may be used as the artificial neural network, and the artificial neural network in which two Bi-LSTM layers (Bi-LSTM layer-1 and Bi-LSTM layer-2) are stacked may be used to extract the accurate ECG data according to the change pattern of the SCG signal in a wide time segment.

When the ECG data is extracted, the ECG signal is acquired by converting the ECG data into an analog signal (S27). In addition, a plurality of critical clinical indicators (e.g., time stamps such as P, Q, R, S, T, RR interval, and QRS segment length) may be extracted from the extracted ECG data. At this point, as the artificial neural network is learned using the ECG signal whose R peak is synchronized with a peak of the SCG signal, the acquired ECG signal is output as the ECG signal whose R peak is synchronized with the peak of the SCG signal.

The method according to the present disclosure may be implemented by a computer program stored in a medium for execution by a computer. Here, the computer-readable medium may be any available medium accessible by the computer and may also include all computer storage media. The computer storage media may include both volatile and nonvolatile, and removable and non-removable media implemented by any method or technique for storing information such as computer-readable instructions, data structures, program modules or other data, and may include a read only memory (ROM), a random-access memory (RAM), a compact disk (CD)-ROM, a digital video disk (DVD)-ROM, a magnetic tape, a floppy disk, an optical data storage device, and the like.

Although the present disclosure has been described with reference to the embodiments shown in the drawings, this is only illustrative, and those skilled in the art will understand that various modifications and equivalent other embodiments are possible therefrom.

Accordingly, the true technical scope of the present disclosure should be defined by the technical spirit of the appended claims.

What is claimed is:

1. An electrocardiogram (ECG) monitoring device comprising:
  a processor; and
  a memory coupled to the processor,
  wherein the processor performs a method comprising:
    acquiring a vibration signal, including a heart vibration of a person to be observed, by detecting a vibration transmitted through an instrument in a non-contact or non-invasive method using at least one vibration meter sensor attached to the instrument at which the person to be observed is positioned;
    extracting a seismocardiography signal (SCG signal) generated by receiving the vibration signal and filtering a predetermined frequency band from the received vibration signal; and
    estimating a pattern of the SCG signal and generating an electrocardiogram signal (ECG signal) of a pattern corresponding to the estimated pattern of the SCG signal using a bidirectional long-short term memory (Bi-LSTM) neural network,
  wherein the extracting the SCG signal further includes:
    performing low pass filtering in order to remove a frequency band exceeding a predetermined first frequency by receiving the vibration signal; and
    performing high pass filtering in order to remove a frequency band lower than a predetermined second frequency by receiving the low-pass-filtered signal
  wherein the Bi-LSTM neural network is learned in advance using a learning SCG signal and a learning ECG signal synchronized so that a peak of the learning SCG signal and an R peak of the learning ECG signal corresponding thereto in learning data including a plurality of learning SCG signals and a plurality of learning ECG signals corresponding thereto acquired in advance appear at the same time point.

2. The ECG monitoring device of claim 1, wherein the synchronized learning SCG signal and learning ECG signal are synchronized through:
  cross-correlating the learning SCG signal and the learning ECG signal corresponding thereto while shifting one of the learning SCG signal and the learning ECG signal corresponding thereto in the learning data within a predetermined range on a time axis upon learning;
  acquiring a synchronous time difference by detecting a time point at which the largest correlation value is calculated; and
  shifting the learning SCG signal or the learning ECG signal corresponding thereto according to the synchronous time difference.

3. The ECG monitoring device of claim 2, wherein the synchronized learning SCG signal and learning ECG signal are synchronized by the synchronous time difference acquired according to a time point at which the largest correlation value is calculated by detecting a plurality of peaks of the learning SCG signal and a plurality of R peaks of the learning ECG signal corresponding thereto and performing a cross-correlation at a time point at which positions of the peak of the learning SCG signal and the R peak of the learning ECG signal detected within the predetermined range are matched.

4. The ECG monitoring device of claim 1, wherein the generating of the ECG signal includes generating the ECG signal having the R peak at the same time point as that of the peak of the SCG signal according to the Bi-LSTM neural network learned in advance using the synchronized learning SCG signal and learning ECG signal.

5. The ECG monitoring device of claim 4, wherein the generating of the ECG signal includes:
sampling the SCG signal at a predetermined sampling rate and converting the sampled SCG signal into SCG data; and
estimating a pattern change of the SCG data, which is time-series data, over time and acquire ECG data having a pattern corresponding to the estimated pattern change by being implemented as the Bi-LSTM neural network learned in advance using the synchronized learning SCG signal and learning ECG signal.

6. The ECG monitoring device of claim 5, wherein the generating of the ECG signal further includes acquiring the ECG signal by receiving the ECG data and converting the received ECG data into an analog signal.

7. The ECG monitoring device of claim 6, wherein the generating of the ECG signal further includes extracting a plurality of predetermined clinical indicators by analyzing the ECG data.

8. The ECG monitoring device of claim 1, wherein the filtering a predetermined frequency band further includes:
measuring and storing a frequency component of a noise of the vibration meter sensor to perform an adaptive filtering,
controlling the predetermined first frequency and the predetermined second frequency,
moving a sliding window in chronological order with respect to SCG data transmitted from a sampling unit, and
transmitting the SCG data to the Bi-LSTM,
wherein a size of the sliding window is set to a size of two or more periods of the SCG signal.

9. The ECG monitoring device of claim 8, wherein the extracting of the SCG signal further includes setting the first frequency and the second frequency according to at least one of a noise of the at least one vibration meter sensor itself and a noise generated in surrounding environment of the instrument.

10. An electrocardiogram (ECG) monitoring method performed by a processor coupled to a memory, the method comprising:
acquiring a vibration signal, including a heart vibration of a person to be observed, by detecting a vibration transmitted through an instrument in a non-contact or non-invasive method using at least one vibration meter sensor attached to the instrument at which the person to be observed is positioned;
extracting a seismocardiography (SCG) signal generated by receiving the vibration signal and filtering a predetermined frequency band from the received vibration signal; and
estimating a pattern of the SCG signal and generating an ECG signal of a pattern corresponding to the estimated pattern of the SCG signal using a bidirectional long-short term memory (Bi-LSTM) neural network learned in advance,
wherein the extracting of the SCG signal further includes:
performing low pass filtering in order to remove a frequency band exceeding a predetermined first frequency by receiving the vibration signal; and
performing high pass filtering in order to remove a frequency band lower than a predetermined second frequency by receiving the low-pass-filtered signal, and
wherein the Bi-LSTM neural network is learned in advance using a learning SCG signal and a learning ECG signal synchronized so that a peak of the learning SCG signal and an R peak of the learning ECG signal corresponding thereto in learning data including a plurality of learning SCG signals and a plurality of learning ECG signals corresponding thereto acquired in advance appear at the same time point.

11. The method of claim 10, wherein the synchronized learning SCG signal and learning ECG signal are synchronized through:
cross-correlating the learning SCG signal and the learning ECG signal corresponding thereto while shifting one of the learning SCG signal and the learning ECG signal corresponding thereto in the learning data within a predetermined range on a time axis upon learning;
acquiring a synchronous time difference by detecting a time point at which the largest correlation value is calculated; and
shifting the learning SCG signal or the learning ECG signal corresponding thereto according to the synchronous time difference.

12. The method of claim 11, wherein the cross-correlating includes:
detecting a plurality of peaks of the learning SCG signal and a plurality of R peaks of the learning ECG signal corresponding thereto; and
performing a cross-correlation at a time point at which positions of the peak of the learning SCG signal and the R peak of the learning ECG signal detected within the predetermined range are matched.

13. The method of claim 10, wherein the generating of the ECG signal includes generating the ECG signal having the R peak at the same time point as that of the peak of the SCG signal according to the Bi-LSTM neural network learned in advance using the synchronized learning SCG signal and learning ECG signal.

14. The method of claim 13, wherein the generating of the ECG signal includes:
sampling the SCG signal at a predetermined sampling rate and converting the sampled SCG signal into SCG data; and
estimating a pattern change of the SCG data, which is time-series data, over time and acquiring ECG data having a pattern corresponding to the estimated pattern change by being implemented as a bidirectional long-short term memory (Bi-LSTM) neural network learned in advance using the synchronized learning SCG signal and learning ECG signal.

15. The method of claim 14, wherein the generating of the ECG signal further includes acquiring the ECG signal by receiving the ECG data and converting the received ECG data into an analog signal.

16. The method of claim 14, wherein the generating of the ECG signal further includes extracting a plurality of predetermined clinical indicators by analyzing the ECG data.

17. The method of claim 10, wherein the filtering a predetermined frequency band further includes:
measuring and storing a frequency component of a noise of the vibration meter sensor to perform an adaptive filtering,
controlling the predetermined first frequency and the predetermined second frequency,
moving a sliding window in chronological order with respect to SCG data transmitted from a sampling unit, and
transmitting the SCG data to the Bi-LSTM,
wherein a size of the sliding window is set to a size of two or more periods of the SCG signal.

18. A non-transitory computer-readable medium containing instructions which when executed on a processor performs a method for monitoring an electrocardiogram (ECG), the method comprising:
  acquiring a vibration signal, including a heart vibration of a person to be observed, by detecting a vibration transmitted through a vibration meter sensor attached to an instrument at which the person to be observed is positioned, wherein the vibration meter sensor does not directly contact with a body of the person;
  extracting a seismocardiography (SCG) signal generated by receiving the vibration signal and filtering a predetermined frequency band from the received vibration signal, wherein the filtering a predetermined frequency band from the received vibration signal further includes:
    performing low pass filtering in order to remove a frequency band exceeding a predetermined first frequency by receiving the vibration signal, and
    performing high pass filtering in order to remove a frequency band lower than a predetermined second frequency by receiving the low-pass-filtered signal; and
  estimating a pattern of the SCG signal and generating an ECG signal of a pattern corresponding to the estimated pattern of the SCG signal using a bidirectional long-short term memory (Bi-LSTM) neural network learned in advance,
  wherein the Bi-LSTM neural network is learned in advance using a learning SCG signal and a learning ECG signal synchronized so that a peak of the learning SCG signal and an R peak of the learning ECG signal corresponding thereto in learning data including a plurality of learning SCG signals and a plurality of learning ECG signals corresponding thereto acquired in advance appear at the same time point.

19. The non-transitory computer-readable medium of claim 18, wherein the extracting the SCG signal includes:
  moving a sliding window in chronological order with respect to SCG data transmitted from a sampling unit, and
  transmitting the SCG data to the Bi-LSTM,
  wherein a size of the sliding window is set to a size of two or more periods of the SCG signal.

* * * * *